(12) United States Patent
LeLorier

(10) Patent No.: US 10,070,824 B2
(45) Date of Patent: Sep. 11, 2018

(54) METHOD OF DETECTING AND PREDICTING NEUROCARDIOGENIC SYNCOPE

(71) Applicant: Paul LeLorier, Mandeville, LA (US)

(72) Inventor: Paul LeLorier, Mandeville, LA (US)

(73) Assignee: PHYSIOVOYANCE, LLC, Mandeville, LA (US)

( * ) Notice: Subject to any disclaimer, the term of this patent is extended or adjusted under 35 U.S.C. 154(b) by 812 days.

(21) Appl. No.: 14/089,431

(22) Filed: Nov. 25, 2013

(65) Prior Publication Data

US 2015/0148698 A1  May 28, 2015
US 2017/0181710 A9  Jun. 29, 2017

Related U.S. Application Data

(63) Continuation-in-part of application No. 12/998,056, filed as application No. PCT/US2009/056734 on Sep. 11, 2009, now abandoned.

(Continued)

(51) Int. Cl.
*A61B 5/00* (2006.01)
*A61B 5/08* (2006.01)
*A61B 5/091* (2006.01)

(52) U.S. Cl.
CPC .......... *A61B 5/7275* (2013.01); *A61B 5/0809* (2013.01); *A61B 5/0816* (2013.01); *A61B 5/091* (2013.01); *A61B 5/746* (2013.01)

(58) Field of Classification Search
None
See application file for complete search history.

(56) References Cited

U.S. PATENT DOCUMENTS

2003/0139780 A1* 7/2003 Markowitz ........ A61N 1/36521
607/17
2004/0039263 A1* 2/2004 Bardy .................. A61B 5/0031
600/300

(Continued)

OTHER PUBLICATIONS

Kamiya, Atsunori, et al. "Low-frequency oscillation of sympathetic nerve activity decreases during development of tilt-induced syncope preceding sympathetic withdrawal and bradycardia." (2005) American Journal of Physiology—Heart and Circulatory Physiology 289. 4: H1758-H1769.*

(Continued)

*Primary Examiner* — Jacqueline Cheng
*Assistant Examiner* — Jairo Portillo
(74) *Attorney, Agent, or Firm* — Roy Kiesel Ford Doody & Thurmon, APLC

(57) ABSTRACT

A method of detecting an early onset of neurocardiogenic syncope in a patient uses respiratory functions as a predictor of the syncope. According to the method, at least one sample of baseline minute ventilation, tidal volume and respiratory rate of the patient is obtained. The detection unit is set to detect an increase in tidal volume and in minute ventilation over a predetermined respiratory period. The detecting unit also detects any rate of change in respiratory rate and sends a signal to a microprocessor to determine whether the increase in minute ventilation is a sole function of increased tidal volume. The impending syncope is diagnosed if variance in respiratory rate is less than 25% in relation to the sampled baseline during the predetermined period of time.

16 Claims, 6 Drawing Sheets

Related U.S. Application Data

(60) Provisional application No. 61/096,494, filed on Sep. 12, 2008.

(56) References Cited

U.S. PATENT DOCUMENTS

| | | | | |
|---|---|---|---|---|
| 2004/0098060 A1* | 5/2004 | Ternes | ................ | A61N 1/3708 607/17 |
| 2007/0070800 A1* | 3/2007 | Virag | ................ | A61B 5/02116 365/244 |

OTHER PUBLICATIONS

Lipsitz, Lewis A., et al. "Vasomotor instability preceding tilt-induced syncope: does respiration play a role?." Journal of Applied Physiology 83.2 (1997): 383-390.*

Benjamin Lebwohol, et al; "Risk of Dementia in Patients with Celiac Disease: A Population-Based Cohort Study"; Journal of Alzheimer's Disease 49 (2016) 179-185; IOS Press.

Richard E. Smalley; "Discovering the Fullerenes" Nobel Lecture, Dec. 7, 1996; Center for Nanoscale Science and Technology, Rice Quantum Institute, and Departments of Chemistry and Physics, Rice University, Houston, Texas 77005, USA.

* cited by examiner

METHOD OF DETECTING AND PREDICTING NEUROCARDIOGENIC SYNCOPE

CROSS-REFERENCE TO RELATED APPLICATIONS

This application is a continuation-in-part of my co-pending application Ser. No. 12/998,056 filed on Mar. 10, 2011 entitled "Pacemaker with Neurocardiogenic Syncope Detection and Therapy Utilizing Minute Ventilation Input," which is based on my Provisional Application Ser. No. 61/096,494, filed on Sep. 12, 2008, the full disclosures of which are incorporated by reference herein and priority of which is hereby claimed.

BACKGROUND OF THE INVENTION

Neurocardiogenic syncope (vasovagal syncope, the common "fainting spell") is a common but complex physiologic disorder. An estimated 6% of the population are recurrent fainters. The condition is marked by a sudden drop in heart rate and blood pressure, resulting in decreased cerebral perfusion and subsequent loss of consciousness and postural tone. This condition is unpleasant and limiting for the patient as well as potentially dangerous; unexpected episodes of syncope may result in injury from falls. In addition, when frequent, it can lead to disability due to prohibitions on driving as well as certain types of employment and activities. Behavioral treatment for recurrent neurocardiogenic syncope has been limited to lifestyle limitation, avoidance behaviors and abortive maneuvers, and liberalization of fluid and sodium intake. Medical therapy has been limited to selective serotonin reuptake inhibitors and the "off label" use of fludrocortisone, a mineralocorticoid that enhances sodium and water retention. The latter therapy is often unacceptable in older patients with preexisting heart disease or hypertension.

Given the limitations of medical and behavioral therapy, some consideration has been given to the role of cardiac pacemakers in treating neurocardiogenic syncope. Since an abrupt drop in heart rate is a prominent feature of most neurocardiogenic syncopal episodes, prior devices and algorithms have focused on various "rate drop response" algorithms, in which the pacemaker detects when the patient's heart rate drops below a lower hysteresis rate and determines whether the rate of decrease in heart rate (dHR/dT) exceeds a predetermined value; if this condition is met, then the pacemaker output is set to the hysteresis rate for a preset time interval. However, as a whole, these therapies have yielded disappointing results.

Given that therapies have yielded inconsistent results, are largely disappointing and pacemakers remain unattractive therapy, the emphasis for this invention is on early recognition of impending syncope and diagnosis of syncopal episodes due to hypotension. Although monitoring of heart rate and rhythm is accomplished simply with a set of three leads applied to the chest (as is used on telemetry units and outpatient monitoring), there is as of yet no practical way of monitoring of intracranial blood flow, the final common pathway that is interrupted when syncope occurs. Additionally, monitoring of systemic blood pressure on a continuous basis, a less than ideal surrogate for intracranial blood flow, is also impractical or difficult in ambulatory individuals. The desire to monitor intracranial blood flow extends beyond diagnosis of patients with recurrent syncope; it also applies to monitoring of such individuals as fighter pilots, test pilots, in aerospace applications, hyperbaric situations and soldiers or first responders in the field.

Some known techniques involve head up tilt table testing to approximate the hemodynamic changes seen during neurocardiogenic syncope. Previous investigations have noted that, in addition to decreases in heart rate and blood pressure, changes in breathing patterns may also occur before fainting. Subjects have been observed to yawn, sigh, or hyperventilate before syncope, suggesting that alterations in respiration may accompany sudden changes in autonomic control of the heart and peripheral vasculature.

The causal relationship between respiratory variation and neurocardiogenic syncope has been unclear. Vasomotor instability preceding syncope has been previously discussed; however, early work did not show a convincing relationship between respiration and syncope in healthy volunteers. Studies using indirect measurement of minute ventilation and complex demodulation have demonstrated that hyperpnea precedes increases in cardiac vagal tone and subsequent decrease in intracranial blood flow and tilt-induced syncope in healthy volunteers. Prior work has shown excellent correlation between exhaled carbon dioxide levels and cerebral blood flow. Previous work also suggests a very reproducible pattern of changes in tidal volume without accompanying changes in respiratory rate, which very reliably predict impending syncope (real-time), diagnose a syncopal event as having occurred (after the fact) and act as an excellent surrogate of decreased cerebral perfusion.

The present invention contemplates elimination of drawbacks associated with prior methods and provision of a method of detecting neurocardiogenic syncope early enough so that avoidance maneuvers can be undertaken or, as of yet not described therapies can be instituted.

SUMMARY OF THE INVENTION

It is, therefore, an object of the present invention to provide a method of detecting the onset of neurocardiogenic syncope at an early stage.

It is another object of the invention to provide a method of predicting the onset of syncope using heart rate and ventilation sensors.

These and other objects of the invention are achieved through a provision of a method including the steps of detecting a series of intrinsic depolarizations of the heart; detecting minute ventilation and respiratory rate; sampling baseline minute ventilation and respiratory rate; detecting an increase in minute ventilation over a predetermined period of time that satisfies a programmed criteria; detecting any rate of change in respiratory rate; determining whether the change in minute ventilation is a sole function of increased tidal volume; and diagnosing impending syncope if minute ventilation criteria are met.

The increase in minute ventilation may be determined to be the result of increased tidal volume, with a relatively fixed respiratory rate.

The determination of baseline minute ventilation and is components, tidal volume and respiratory rate may be determined by measurement of transthoracic impedance or by direct measurement of exhaled volumes and respiratory rate.

The increase in tidal volume may be defined as being more than a 75% increase from baseline. The fixed respiratory rate may be defined as a less than 25% variance in respiratory period, R. The method also includes storing at least one data item related to the step of detecting an increase in minute ventilation.

The above summary of the invention is included in order to provide a basic understanding of some aspects and features of the invention. This summary is not an extensive overview of the invention and as such it is not intended to particularly identify key or critical elements of the invention or to delineate the scope of the invention. Its sole purpose is to present some concepts of the invention in a simplified form as a prelude to the more detailed description that is presented below.

BRIEF DESCRIPTION OF THE DRAWINGS

The accompanying drawings, which are incorporated in and constitute a part of this specification, exemplify the embodiments of the present invention and, together with the description, serve to explain and illustrate principles of the invention. The drawings are intended to illustrate major features of the exemplary embodiments in a diagrammatic manner. The drawings are not intended to depict every feature of actual embodiments nor relative dimensions of the depicted elements, and are not drawn to scale.

DETAIL DESCRIPTION OF THE INVENTION

Figures 1A, 1B:
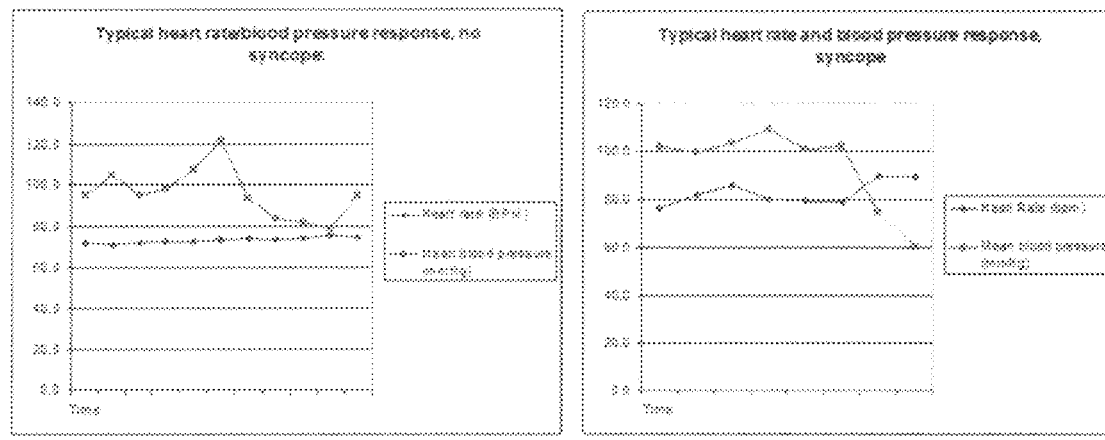
FIGS. 1A and 1B are graphical depictions showing heart rate and blood pressure response with and without syncope.

According to one aspect of the invention, a computer readable medium for storing instructions for performing a method, is provided that includes instructions for detecting a series of intrinsic depolarizations of a heart; detecting minute ventilation and respiratory rate; sampling baseline minute ventilation and respiratory rate; detecting an increase in minute ventilation over a predetermined period of time that satisfies a programmed criteria; detecting any rate of change in respiratory rate; determining whether the change in minute ventilation is a sole function of increased tidal volume; and diagnosing a syncopal episode as having a hypotensive etiology if minute ventilation criteria are met without accompanying rhythm disturbances. The computer readable medium may also include storing at least one data item related to the step of detecting an increase in minute ventilation.

According to another aspect of the invention, an implanted cardiac or subcutaneous apparatus is provided that includes means for detecting a series of intrinsic depolarizations of a heart; means for detecting minute ventilation and respiratory rate; means for sampling baseline minute ventilation and respiratory rate, detecting an increase in minute ventilation over a predetermined period of time that satisfies a programmed criteria, detecting any rate of change in respiratory rate, and determining whether the change in minute ventilation is a sole function of increased tidal volume; and means for detecting impending syncope or altered cerebral perfusion if minute ventilation criteria are met. The implanted apparatus may also include means for storing at least one data item related to the step of detecting an increase in minute ventilation.

This invention provides a syncope detection method, which uses respiratory input to detect impending neurocardiogenic or hypotensive syncope is described. The methodology provides both a diagnostic option for patients with undiagnosed syncope when coupled to modified event monitors, and diverse monitoring options for individuals in whom monitoring of brain perfusion would be desirable (pilots, astronauts, divers, soldiers, etc.).

The inventor discovered that a 2 to 3 fold increase in minute ventilation precedes the drop in heart rate and blood pressure in tilt-induced neurocardiogenic syncope. This increase in minute ventilation is driven exclusively by increases in tidal volume (TV) rather than respiratory rate, which allows for easy distinction between impending neurocardiogenic syncope and other physiologic causes of increased minute ventilation (for example, exercise, pain, anxiety, primary respiratory distress, and heart failure). The inventor has also previously described an excellent correlation between cerebral blood flow and end-tidal carbon dioxide. As end-tidal carbon dioxide decreases, so does the cerebral blood flow. The mechanism for the link is not clear, but may have to do with the role of carbon dioxide as a cerebral vasoregulator. This is illustrated in FIG. 6 and has been previously published by the inventor.

Figures 2A, 2B:
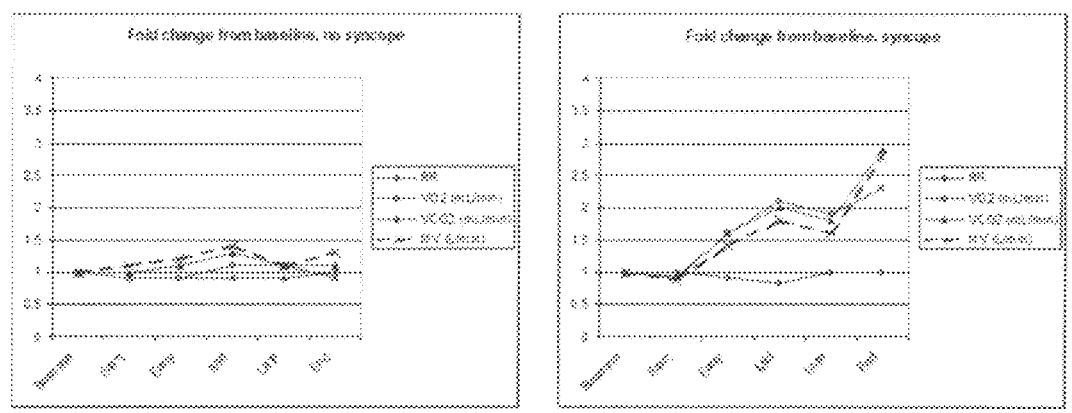
FIGS. 2A and 2B are graphical depictions showing fold change from baseline without (FIG. 2A) and with (FIG. 2B) syncope.
Figure 3:
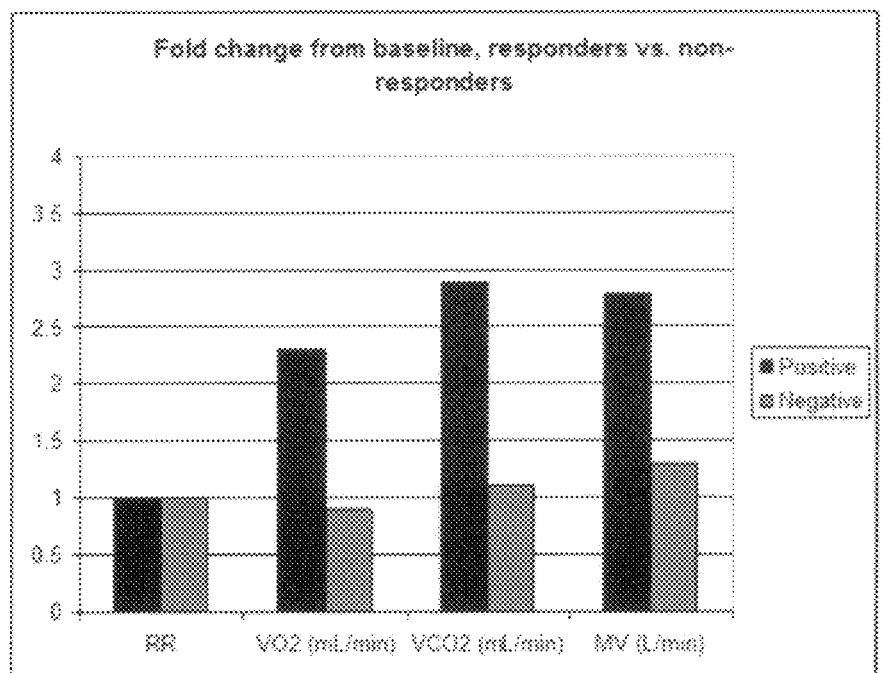
FIG. 3 is a graphical depiction change in minute ventilation from baseline for responders and non-responders.

With reference to FIGS. 1A and 1B, a typical heart rate and blood pressure response is shown in patients without syncope (FIG. 1A) and with syncope (FIG. 1B). As shown in FIGS. 1A and 1B, syncope is marked by a sudden drop in heart rate and blood pressure which results in decreased cerebral perfusion and subsequent loss of consciousness and postural tone. As shown in FIGS. 2A, 2B and FIG. 3, during syncope, there is an increase in minute ventilation (MV) and tidal volume (VO2/VCO2) while the respiration rate remains the same.

The syncope detection method utilizes respiratory input for early detection of impending syncope, with subsequent warning or triggered therapies or maneuvers to prevent development of syncope. When the detected minute ventilation exceeds a predetermined threshold value without a corresponding increase in respiratory rate, the episode gets labeled as impending syncope and either stored for further analysis or transmitted real-time to the subject and/or remote monitoring stations via audible and/or vibratory alarm.

Figure 4:
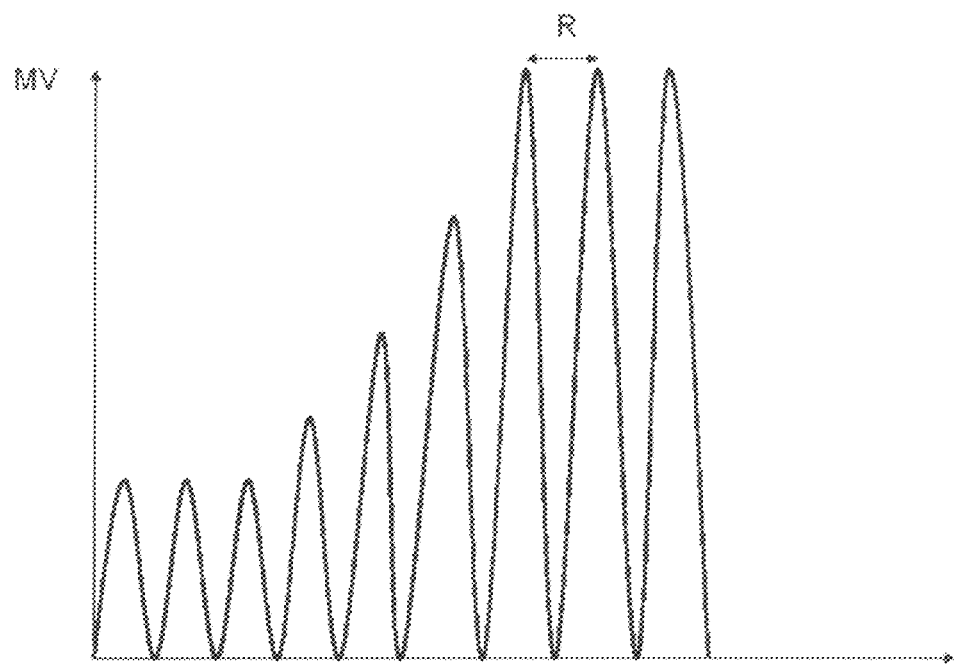
FIG. 4 is a graphical depiction of minute ventilation during syncope.

FIG. 4 shows the typical evolution of minute ventilation signal (MV) with respect to time in a patient with neurocardiogenic syncope. Note that the respiratory interval (R) remains fixed, while the tidal volume (TV, or TE) increases substantially. As described above, MV is a signal which may be directly obtained from measuring thoracic impedance. Oscillations in thoracic impedance with respect to time allow for the derivation of TV and R.

The measurement of minute ventilation can be obtained directly by measuring exhaled volumes and rate, or indirectly by changes in thoracic impedance between two electrodes on the skin. The impedance is then measured in response to the application of constant current (e.g., approximately 200 mA) at a fixed frequency (e.g., usually 8 Hz). From this, one can determine the respiratory period (R), or respiratory rate (breaths per minute). The tidal volume (TV) is represented by the area under the curve, and the minute ventilation is the product of (R×TV)/min.

Figure 5:
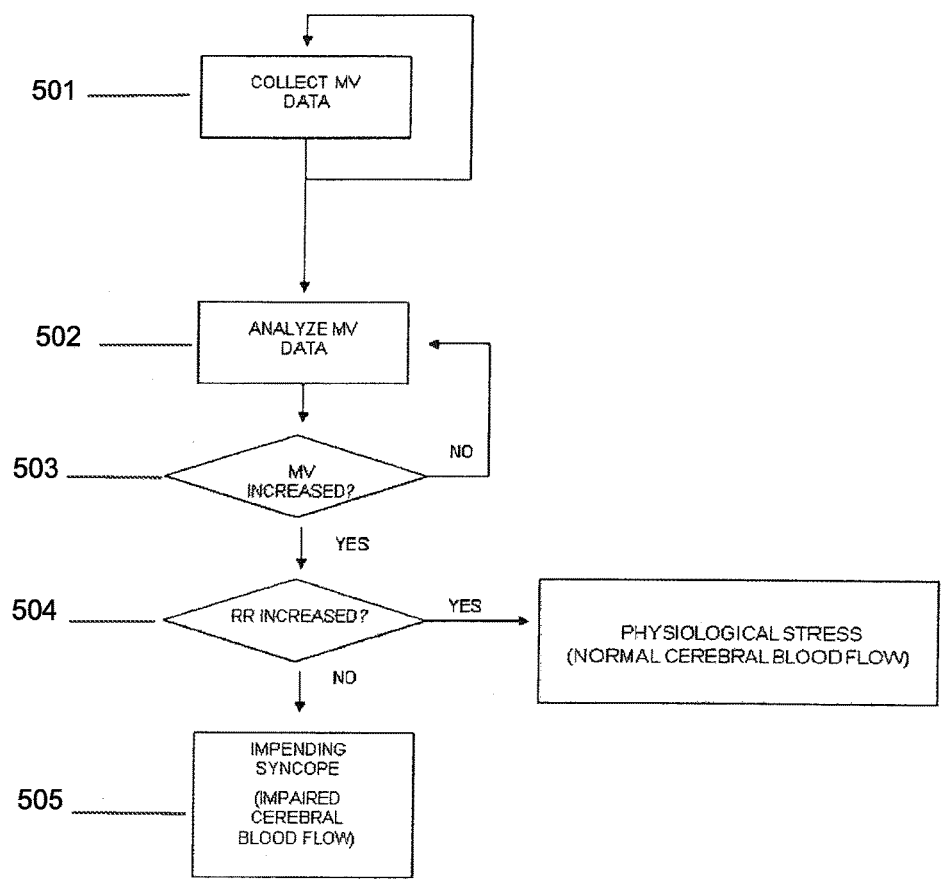
FIG. 5 is a flow chart of a process for detecting syncope and/or impending syncope.

FIG. 5 illustrates a process for detecting decreasing cerebral perfusion, and/or impending syncope and/or syncope. The process is described in the context of a process for measuring transthoracic impedance, such as in the case wearable external monitors, or directly measuring tidal volumes, as could be use with aerospace and hyperbaric applications. It will be appreciated that the method may be used with implantable medical devices as well. In addition, it will be appreciated that the process may vary. The process may include additional steps or fewer steps and the order of the steps may differ.

Minute ventilation, either by transthoracic impedance measurements or by spirometry, is being constantly sampled in step 501 and analyzed in step 502. If an increase in minute ventilation is detected in step 503, then the respiratory interval is analyzed in step 504. The respiratory interval may be analyzed over a fixed period of time (e.g., any time period or range of time periods between about 10 seconds and about 5 minutes, including less than ten seconds and more than 5 minutes). If the increased minute ventilation is not accompanied by a decrease in respiratory interval (e.g., the respiratory interval does not decrease for a predetermined period of time, e.g., any time period or range of time periods between about 10 seconds and about 5 minutes, including less than ten seconds and more than 5 minutes), then the conditions for impending syncope have been met, as shown in step 505.

If, on the other hand, the respiratory interval is decreased, then the heart rate and any additional data are analyzed (such as accelerometer or contextual information). Increased minute ventilation, decreased respiratory interval, increased heart rate and detected acceleration indicate increased physical activity or stressor other than decreased cerebral hypoperfusion in step 506. Alternatively, increases in minute ventilation, decreased respiratory interval, heart rate and no detected acceleration would indicate increased physiologic stress without physical activity (for example, heart failure, anxiety, or respiratory distress); this information may be subsequently used for diagnostic purposes. It will be appreciated that the detection algorithm may be applied without the use of accelerometer data. It will also be appreciated that minute ventilation may be based upon measured $MVO_2$.

Figure 6A:
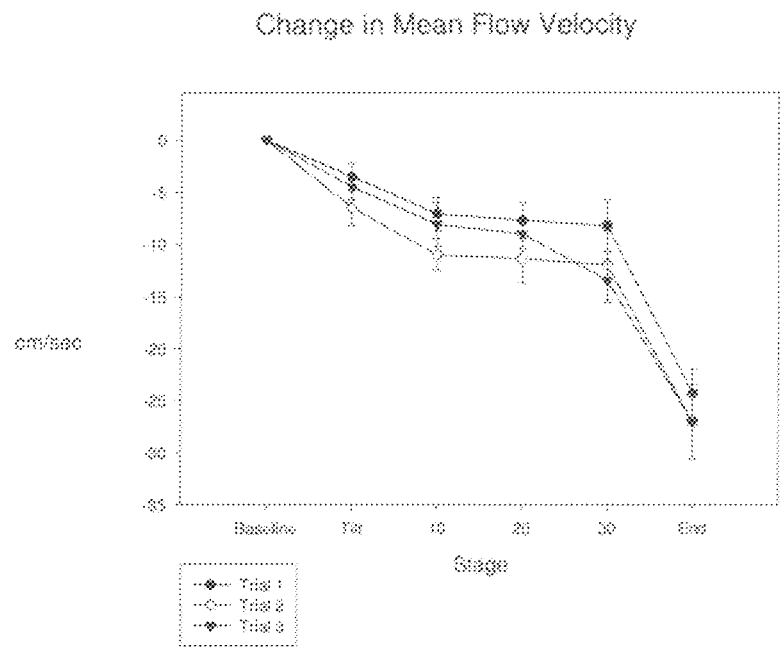
FIG. 6A graphically illustrates change in mean flow velocity in three exemplary trials, and FIG. 6B graphically illustrates change in End Tidal $CO_2$ measured in normal subjects in whom hypotension was induced with a combination of head-up tilt and lower body negative pressure over three trial on three different days. Also shown are direct measurements of cerebral blood flow in the same subjects at the same times and distinct correlation between cerebral blood flow and End Tidal $CO_2$.
Figure 6B:
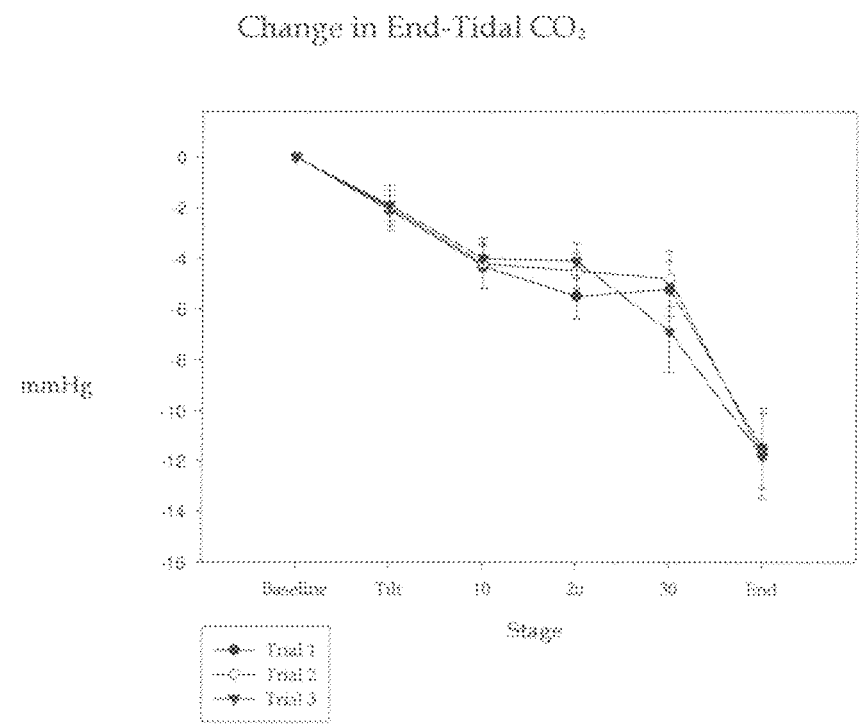

FIG. 6A illustrates change in mean flow velocity and FIG. 6B illustrates changes in end tidal carbon dioxide ($CO_2$) measured in normal subjects in whom hypotension was induced with a combination of head-up tilt and lower body negative pressure over three trial on three different days. Also shown are direct measurements of cerebral blood flow in the same subjects at the same times. The graph illustrates excellent correlation between cerebral blood flow and End Tidal $CO_2$ is shown.

The detection method described above may be applied to any monitoring device, internal or external, portable or fixed, which is outfitted to measure minute ventilation and respiratory rate at a minimum, with additional possible enhancements of accelerometer and heart rate.

It should be understood that processes and techniques described herein are not inherently related to any particular apparatus and may be implemented by any suitable combination of components. Further, various types of general purpose devices may be used in accordance with the teachings described herein. It may also prove advantageous to construct specialized apparatus to perform the method steps described herein.

Figure 7:
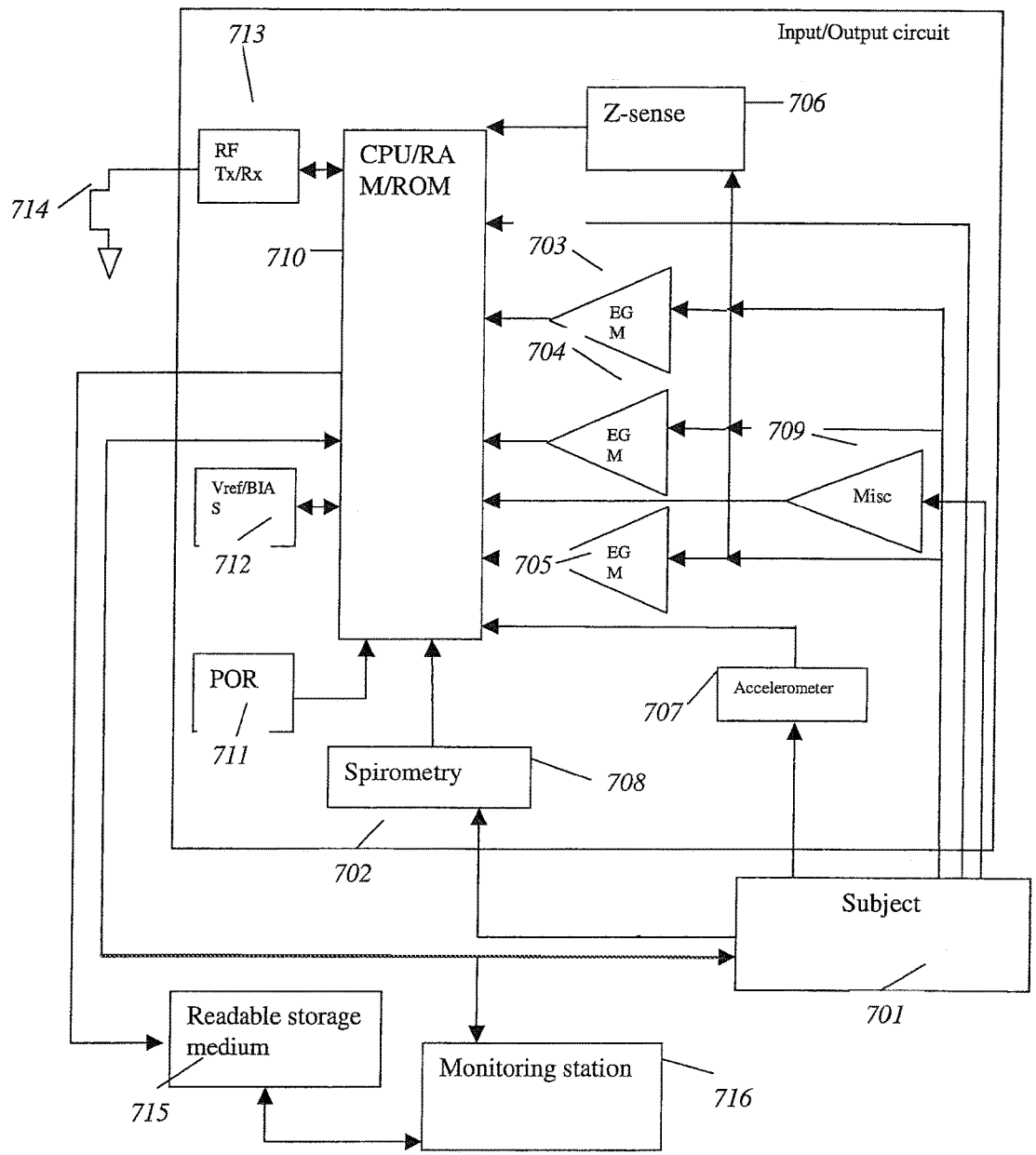
FIG. 7 is a block diagram illustrating a worn or fixed device that processes various signals from a subject, processes them, stores them and provides real-time feedback to the subject and/or to an external monitoring system.

FIG. 7 is a block diagram illustrating the constituent components of the device in accordance with one embodiment of the invention. Any one embodiment may contain some, or all of the input signals represented here, depending on the application for which the build is required. It will be understood by those skilled in the art that the electrical components represented in FIG. 7 are powered by an appropriate battery supply or external power source (not shown). The input devices are connected to a subject 701.

The input/output circuit 702 contains the operating input and output analog circuits for digital controlling and timing circuits necessary for the detection of electrical signal derived from the heart, such as the surface cardiac electrogram derived from three leads 703, 704 and 705. Thoracic impedance (Z-sense) is derived from current between the surface leads 706. Accelerometer data 707 is derived from a piezoelectric crystal within the unit in the case of portable applications. Additional input is derived from spirometry data 708 in some applications as well as contextual and symptoms reported by the subject via means of voice recording or text input 709. It will be understood by those skilled in the art that various forms of input devices are possible, including microphones and keypads, but they are not illustrated here. These input feed into a microprocessor or microcomputer unit 710. It will be understood by those skilled in the art that the microprocessor unit comprises an on-board circuit and an off-board circuit. On-board circuit includes a microprocessor, a system clock, an on-board RAM and ROM. Off-board circuit includes an off-board RAM/ROM unit providing additional memory. These are not illustrated.

Additional input into the microcomputer unit will be from a power-on-reset circuit (POR) 711 which serves to initialize the unit with programmed default settings on power-up, and reset the program values to default states upon detection of an insufficient power supply or transiently in the presence of certain undesirable conditions such as unacceptably high electromagnetic interference. (EMI), for example. A Vref/Bias circuit 712 generates a stable voltage reference and bias currents for the analog circuits of input/output circuit 702.

An antenna 714 is connected to input/output circuit 702 for purposes of uplink/downlink telemetry through a radio frequency (RF) Transmitter/Receiver Circuit (RF TX/RX) 713. Uplink and downlink telemetry transmission of programming commands and analog and digital data between antenna 714 and an external device, such a monitoring station 716 or storage media 715, can be accomplished employing any of the hardware and operating systems known in the art. Communication between the input/output circuit 702 and storage medium 715 and monitoring station 716 may also be accomplished by direct, wired connections.

The input/output circuit can additionally provide feedback 710 to the subject 701 in the form of visual and/or auditory and/or vibratory signals.

Figure 8:
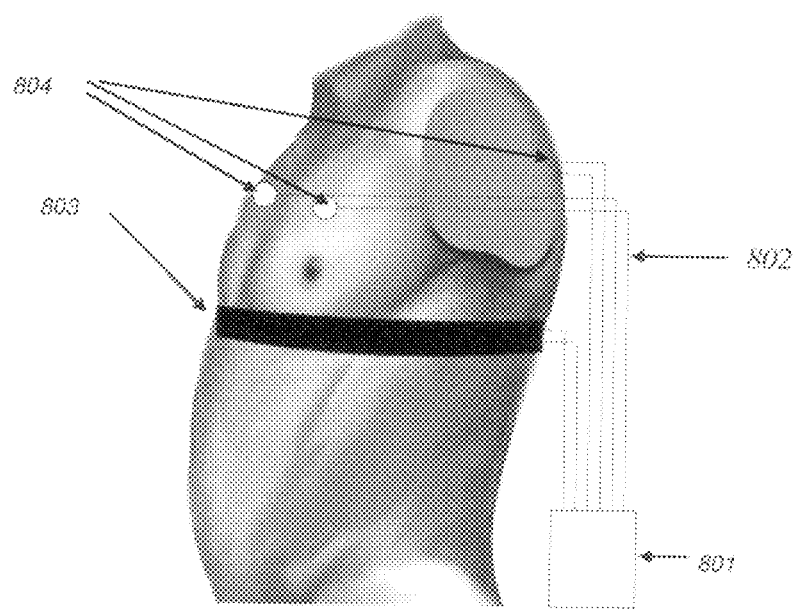
FIG. 8 demonstrates an example of a portable version of the unit at its most simplest. Spirometry data is not collected in this example.

FIG. 8 illustrates a non-spirometric application of the invention wherein thoracic impedance, respiratory rate and electrograms are obtained, recorded, stored and transmitted in a portable device 801 incorporating the input/output circuit 702 mentioned previously. Electrodes 804 are placed on the subject's chest and back for measurement of thoracic impendance and, optionally, cardiac electrograms. A belt 803 around the chest will serve the functions of respirometry independent of thoracic impedance and contain an antenna which would increase the range of the unit. In this example, the input/output unit 801 is wired to the subject 802 but transmitting to a storage unit and monitoring unit wirelessly.

The present invention has been described in relation to particular examples, which are intended in all respects to be illustrative rather than restrictive. Those skilled in the art will appreciate that many different combinations will be suitable for practicing the present invention. Moreover, other implementations of the invention will be apparent to those skilled in the art from consideration of the specification and practice of the invention disclosed herein. Various aspects and/or components of the described embodiments may be used singly or in any combination. It is intended that the specification and examples be considered as exemplary only, with a true scope and spirit of the invention being indicated by the following claims.

I claim:

1. A method of detecting an impending neurocardiogenic syncope in a patient, comprising the steps of:
    obtaining at least one sample of baseline minute ventilation, tidal volume and respiratory rate of the patient;
    detecting an increase in tidal volume over a predetermined period of respiration;
    detecting an increase in minute ventilation over said predetermined period of respiration;
    detecting any change in respiratory rate over said predetermined period of respiration;
    storing at least one data associated with the increase in minute ventilation; and
    detecting impending syncope when
    (a) the increase in minute ventilation is attributable to an increase in tidal volume; and
    (b) the change in respiratory rate is less than 25% in relation to the at least one sampled baseline respiratory rate during the predetermined period of respiration, wherein the steps of detecting an increase in minute ventilation, detecting an increase in tidal volume, detecting any change in respiratory rate, and detecting impending syncope each occur, at least in part, in a microprocessor.

2. The method of claim 1, comprising a step of generating an alarm signal after the impending syncope is detected.

3. The method of claim 1, wherein the step of obtaining at least one sample of baseline minute ventilation, tidal volume, and respiratory rate of the patient is performed by measuring transthoracic impedance or directly by exhaled volumes.

4. The method of claim 1, wherein impending syncope is detected when the detected increase in tidal volume is more than a 75% increase from the baseline.

5. A non-transitory computer readable medium for storing instructions for performing the method of claim 1 when executed.

6. A method of preventing neurocardiogenic syncope in operators of equipment, comprising the steps of:
    obtaining at least one sample of baseline minute ventilation, tidal volume and respiratory rate of the equipment operator;
    detecting an increase in tidal volume over a predetermined period of respiration of said equipment operator;
    detecting an increase in minute ventilation over said predetermined period of respiration of said equipment operator;
    detecting any change in respiratory rate over said predetermined period of respiration of said equipment operator;
    storing at least one data associated with the increase in minute ventilation; and
    alerting the equipment operator of impending syncope when
    (a) the increase in minute ventilation is attributable to an increase in tidal volume; and
    (b) the change in respiratory rate is less than 25% in relation to the at least one sampled baseline respiratory rate during the predetermined period of respiration, wherein the steps of detecting an increase in minute ventilation, detecting an increase in tidal volume, and detecting any change in respiratory rate each occur, at least in part, in a microprocessor.

7. A method of preventing neurocardiogenic syncope in operators of equipment according to claim 6 wherein the alert to the equipment operator comprises an audible alarm.

8. A method of preventing neurocardiogenic syncope in operators of equipment according to claim 6 wherein the alert to the equipment operator comprises a vibratory alarm.

9. The method of claim 6, wherein the step of obtaining at least one sample of baseline minute ventilation, tidal volume, and respiratory rate of the equipment operator is performed by measuring transthoracic impedance or directly by exhaled volumes.

10. The method of claim 6, wherein the step of alerting the equipment operator of impending syncope is performed only when the detected increase in tidal volume is more than a 75% increase from the baseline.

11. A non-transitory computer readable medium for storing instructions for performing the method of claim 6 when executed.

12. A method of detecting impending neurocardiogenic syncope in a patient, said method comprising:
    obtaining a sample baseline minute ventilation, tidal volume, and respiratory rate from the patient;
    obtaining a second minute ventilation, tidal volume, and respiratory rate from the patient over a predetermined period of time; and
    detecting impending syncope in the patient by
    (a) detecting an increase in minute ventilation, attributable to an increase in tidal volume, between said second minute ventilation and said baseline minute ventilation; and
    (b) detecting a change in respiratory rate between said second respiratory rate and said baseline respiratory rate of less than 25%, wherein the steps of detecting an increase in minute ventilation, detecting a change in respiratory rate, and detecting impending syncope each occur, at least in part, in a microprocessor.

13. The method of claim 12, comprising a step of storing at least one data associated with said increase in minute ventilation.

14. The method of claim 12, wherein the step of obtaining a sample baseline minute ventilation, tidal volume, and respiratory rate of the patient is performed by measuring transthoracic impedance or directly by exhaled volumes.

15. The method of claim 12, wherein the step of detecting impending syncope further comprises detecting if said second tidal volume is more than 75% above the baseline tidal volume.

16. A non-transitory computer readable medium for storing instructions for performing the method of claim 12 when executed.

* * * * *